United States Patent
Anand et al.

(12) 
(10) Patent No.: US 10,849,679 B2
(45) Date of Patent: Dec. 1, 2020

(54) HEAT SINK PARAMETER DETERMINATION APPARATUS

(71) Applicant: KONINKLIJKE PHILIPS N.V., Eindhoven (NL)

(72) Inventors: Ajay Anand, Fishkill, NY (US); Shriram Sethuraman, Woburn, MA (US); Sheng-Wen Huang, Ossining, NY (US); Junbo Li, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 364 days.

(21) Appl. No.: 15/116,965

(22) PCT Filed: Feb. 3, 2015

(86) PCT No.: PCT/EP2015/052105
§ 371 (c)(1),
(2) Date: Aug. 5, 2016

(87) PCT Pub. No.: WO2015/121098
PCT Pub. Date: Aug. 20, 2015

(65) Prior Publication Data
US 2016/0346031 A1 Dec. 1, 2016

(30) Foreign Application Priority Data

Feb. 11, 2014 (WO) ................. PCT/CN2014/071964
May 2, 2014 (EP) ...................................... 14166855

(51) Int. Cl.
*A61B 18/14* (2006.01)
*A61N 7/02* (2006.01)
(Continued)

(52) U.S. Cl.
CPC .......... *A61B 18/14* (2013.01); *A61B 18/1492* (2013.01); *A61B 18/1815* (2013.01);
(Continued)

(58) Field of Classification Search
CPC ... A61B 8/5223; A61B 18/14; A61B 18/1492; A61B 18/1815; A61B 2018/00577; A61B 2018/00791; A61N 7/02
See application file for complete search history.

(56) References Cited

U.S. PATENT DOCUMENTS 8,016,757 B2 9/2011 Kaczkowski et al.
9,392,992 B2 7/2016 Hsu et al.
(Continued)

OTHER PUBLICATIONS

Sheeiman, R.,G., et al., "In vivo determination of a modified heat capacity of small hepatocellular carcinomas prior to radiofrequency ablation: Correlation with adjacent vasculature and tumour recurrence", Int. J. Hyperhermia, Mar. 2012; 28(2):122-131.
(Continued)

*Primary Examiner* — Linda C Dvorak
*Assistant Examiner* — Annabeth E Rodriguez
(74) *Attorney, Agent, or Firm* — Sherry Austin

(57) ABSTRACT

The invention relates to a heat sink parameter determination apparatus for determining a parameter of a heat sink like a blood vessel within an object such as a person (3) by minimizing a deviation between a measured temperature distribution, which has preferentially been measured by ultrasound thermometry, and a modeled temperature distribution, wherein the modeled temperature distribution is modeled based on a provided heat source parameter like the location of an ablation needle (2) and the heat sink parameter to be determined by using a given thermal model. This determination of heat sink parameters, which may be geometric and/or flow parameters, considers the real temperature distribution and is thus based on real heat sink influences on the temperature distribution. This can lead to an improved determination of heat sink parameters and hence to a more accurate temperature distribution which may be determined based on the determined heat sink parameters.

15 Claims, 5 Drawing Sheets

(51) Int. Cl.
*A61B 18/18* (2006.01)
*A61B 18/00* (2006.01)

(52) U.S. Cl.
CPC ...... *A61N 7/02* (2013.01); *A61B 2018/00577* (2013.01); *A61B 2018/00642* (2013.01); *A61B 2018/00648* (2013.01); *A61B 2018/00714* (2013.01); *A61B 2018/00791* (2013.01); *A61B 2018/00845* (2013.01); *A61B 2018/00994* (2013.01)

(56) References Cited

U.S. PATENT DOCUMENTS

| | | |
|---|---|---|
| 9,399,148 B2 | 7/2016 | Anand et al. |
| 9,999,789 B2 | 6/2018 | Kuhn |
| 2005/0288666 A1 | 12/2005 | Bertolero et al. |
| 2007/0106157 A1* | 5/2007 | Kaczkowski .......... A61B 5/015 600/438 |
| 2009/0171349 A1* | 7/2009 | Byrd ................ A61B 18/1492 606/41 |
| 2011/0060221 A1* | 3/2011 | Fan ........................ A61B 5/015 600/438 |
| 2013/0296743 A1 | 11/2013 | Lee et al. |

OTHER PUBLICATIONS

Solovchuk, M.A., et al., "Simulation study on acoustic streaming and convective cooling in blood vessels during a high-intensity focused ultrasound thermal ablation", International Journal of Heat and Mass Transfer 55 (2012) 1261-1270.

\* cited by examiner

US 10,849,679 B2

HEAT SINK PARAMETER DETERMINATION APPARATUS

CROSS-REFERENCE TO PRIOR APPLICATIONS

This application is the U.S. National Phase application under 35 U.S.C. § 371 of International Application Serial No. PCT/EP2015/052105, filed on Feb. 3, 2015, which claims the benefit of Chinese Application Serial No. PCT/CN2014/071964, filed on Feb. 11, 2014 and European Patent Application No. 14166855.8, filed May 2, 2014. These applications are hereby incorporated by reference herein.

FIELD OF THE INVENTION

The invention relates to a heat sink parameter determination apparatus, method and computer program for determining a parameter of a heat sink within an object. The invention relates further to a temperature distribution determination apparatus, method and computer program for determining a temperature distribution within the object, which use the determined heat sink parameter. The invention relates also to a heating system comprising the temperature distribution determination apparatus.

BACKGROUND OF THE INVENTION

US 2007/106157 A1 discloses a system for selectively delivering a thermal therapy to a specific mass of tissue. The system comprises a thermal source, an ultrasound imaging probe, a means for identifying when the specific mass of tissue has reached a predetermined temperature, and a controller being adapted to implement the functions of using the thermal source to change a temperature of the specific mass of tissue and collecting a first set of ultrasound data as the specific mass of tissue returns to a previous temperature. The controller is further adapted to implement the functions of using the first set of ultrasound data to determine a thermal diffusivity parameter corresponding to the specific mass of tissue, using the thermal source to change a temperature of the specific mass of tissue to the predetermined value, while collecting a second set of ultrasound data, and determining a length of time required to change the temperature of the specific mass of tissue to the predetermined value. The controller is further adapted to implement the function of using the thermal diffusivity parameter, the second set of ultrasound data, the length of time, and a biological tissue heat transfer model to determine a thermal source magnitude parameter corresponding to the thermal source and the specific mass of tissue, thereby calibrating the biological tissue heat transfer model to the thermal source and the specific mass of tissue.

EP 2 387 963 A1 discloses a temperature distribution determining apparatus for determining a temperature distribution within an object caused by applying energy to the object, wherein the temperature distribution determining apparatus comprises a temperature distribution measuring unit for measuring a spatially and temporally dependent first temperature distribution in the object, while the energy is applied to the object such that the object is heated to a temperature within a first temperature range, and a temperature distribution estimating unit for estimating a spatially and temporally dependent second temperature distribution in the object within a second temperature range, which is different to the first temperature range, based on the spatial and temporal dependence of the measured first temperature distribution.

US 2013/296743 A1 discloses an ultrasound scanner comprising transmitters operable to scan with beams of ultrasound in a scan sequence and a processor configured to create the scan sequence as a function of a therapy plan and to turn off the transmitters for at least a portion of the scan sequence. The ultrasound scanner further comprises a trigger output configured to output triggers to a therapy device, wherein the output triggers are responsive to the scan sequence.

WO 2010/140125 A1 discloses a therapeutic system comprising an ultrasound therapy unit arranged to insonify at least a portion of a body of a patient with high intensity ultrasound and a magnetic resonance imaging unit arranged to acquire magnetic resonance signals from the portion of the body and to reconstruct a thermographic magnetic resonance image from the magnetic resonance signals. The therapeutic system further comprises an ultrasound diagnostic unit arranged to acquire ultrasound signals from the portion of the body and to derive at least one local temperature value from the ultrasound signals.

US 2011/0060221 A1 discloses a temperature distribution determination apparatus for determining a temperature distribution within a person, while a part of the person is ablated during, for instance, a radio frequency (RF) ablation procedure. The temperature distribution determination apparatus is adapted to measure temperature related ultrasound data representing the temperature at different locations within the person and to use these ultrasound data for modeling the temperature distribution within the person with a time-dependent machine-trained model. In an embodiment anatomical ultrasound information is used to indicate blood vessels within the person, wherein this information is used to correct the modeled temperature distribution.

Since different blood vessels, which appear to have the same anatomy as indicated by the anatomical ultrasound information, may influence the temperature distribution differently, the finally determined corrected temperature distribution may be inaccurate.

SUMMARY OF THE INVENTION

It is an object of the present invention to provide a heat sink parameter determination apparatus, method and computer program for determining a parameter of a heat sink within an object, which allows for an improved determination of a temperature distribution. It is a further object of the present invention to provide a temperature distribution determination apparatus, method and computer program for determining a temperature distribution within the object, which use the determined heat sink parameter and therefore allow for a more accurate determination of the temperature distribution. Moreover, it is an object of the present invention to provide a heating system for heating the object, which comprises the temperature distribution determination apparatus.

In a first aspect of the present invention a heat sink parameter determination apparatus for determining a parameter of a heat sink within an object is presented, the heat sink parameter determination apparatus comprises:

a heat sink location providing unit for providing a heat sink location, a temperature distribution measuring unit for measuring a temperature distribution in the object close to the provided heat sink location, a heat source parameter providing unit for providing a parameter of the heat source, which defines the heating of the object, a model providing unit for providing a model describing a temperature distribution in the object, while the object is heated by the heat source, wherein the model depends on the heat sink parameter and the heat source parameter, a parameter determination unit for determining the heat sink parameter by minimizing a deviation between the temperature distribution, which has been measured close to the provided heat sink location, and a modeled temperature distribution, wherein the modeled temperature distribution is modeled based on the provided heat source parameter and the heat sink parameter to be determined by using the provided model.

Since the heat sink parameter is determined by minimizing a deviation between the measured temperature distribution and the modeled temperature distribution, wherein the modeled temperature distribution is modeled based on the provided heat source parameter and the respective heat sink parameter to be determined by using the provided model, the determination of the heat sink parameter considers the real temperature distribution within the object and is thus based on its real influence on the temperature distribution. This can lead to an improved determination of the heat sink parameter and hence to a more accurate temperature distribution, which may be determined based on the determined heat sink parameter.

The temperature distribution measuring unit can be adapted to determine a spatial and/or temporal temperature distribution. The temperature distribution measuring unit comprises preferentially an ultrasound probe for acquiring ultrasound data of the object and an ultrasound thermometry unit for determining the temperature distribution based on the acquired ultrasound data. The ultrasound probe is adapted to send ultrasound waves into the object and receive backscattered ultrasound waves from the object, in order to acquire the ultrasound data. In an embodiment the heat sink is a blood vessel and the ultrasound probe can be able to acquire the ultrasound data in three dimensions, wherein for determining the temperature distribution ultrasound data of one or several planes, which may traverse the blood vessel, may be used. By using the ultrasound probe, which can acquire the ultrasound data in three dimensions, the placement of the one or several planes traversing the vessel can be very flexible.

The heat sink location providing unit can be adapted to determine the heat sink location based on ultrasound data of the object acquired by the ultrasound probe. In particular, the ultrasound probe can be adapted to measure ultrasound data in three dimensions, in order to provide a volume data set in which the heat sink location providing unit can detect the heat sink, especially a blood vessel, by using, for instance, known segmentation techniques. The ultrasound probe can therefore be used for at least two purposes, measuring the temperature distribution and determining the heat sink location, which can lead to a more compact heat sink determination apparatus.

In an embodiment, for determining the heat sink parameter the temperature distribution measuring unit may measure the temperature distribution only close to the provided heat sink location, wherein the measured temperature distribution may be used for determining the heat sink parameter. In an embodiment for determining the heat sink parameter the temperature distribution may be measured close to the provided heat sink location and also at a larger distance from the heat sink location, wherein for determining the heat sink parameter only the temperature distribution may be used, which has been measured close to the heat sink location. The heat source parameter providing unit may be adapted to determine one or several heat source parameters, which define the heating of the object, and to provide the determined one or several heat source parameters, or the heat source parameter providing unit may just be a storing unit, in which previously determined and/or received one or several heat source parameters are stored and from which the one or several heat source parameters can be retrieved for providing the same. The one or several heat source parameters include, for instance, the location of the heat source, the amount of heat delivered to the object, in particular, at which times which amount of heat is delivered to the object, et cetera.

In an embodiment the object is a living being like a person or an animal, the heat sink is a blood vessel and the heat source is an ablation element for ablating a tissue region of the living being. In this case the location of the ablation element may be determined by a localization system like an x-ray localization system, an electromagnetic (EM) localization system, an optical shape sensing (OSS) localization system, et cetera, wherein the location determined by the localization system can be sent to the heat source parameter providing unit, in order to allow the heat source parameter providing unit to provide the determined location as a heat source parameter. Moreover, a heating control unit for controlling the heating by the ablation element can be adapted to send heating information regarding heating times and heating amounts to the heat source parameter providing unit, in order to allow the heat source parameter providing unit to provide this information as heat source parameters. The ablation element can be an RF ablation element, a microwave ablation element, a high intensity focused ultrasound (HIFU) ablation element or any other ablation element being adapted to heat the object.

The parameter determination unit can be adapted to determine one or several heat sink parameters. Moreover, the model providing unit can be adapted to provide a model, which depends on one or several heat sink parameters and/or which depends on one or several heat source parameters. In an embodiment the heat sink parameter determination apparatus is adapted to determine one or several heat sink parameters which include a location of the heat sink within the object and/or, if the heat sink comprises a tubular structure with a flowing fluid, a flow direction and/or a diameter of the tubular structure and/or a flow rate. These heat sink parameters are very well suited for determining an improved temperature distribution. However, the heat sink parameter determination apparatus can also be adapted to alternatively or additionally determine other heat sink parameters.

In another embodiment the heat sink parameter determination apparatus comprises an initial heat sink parameter providing unit for providing an initial heat sink parameter for initializing the provided model, wherein the parameter determination unit is adapted to start the determination of the heat sink parameter with the initialized model. The initial heat sink parameter providing unit can be adapted to provide, for instance, a location of the heat sink and/or, if the heat sink is a tubular structure with a flowing fluid, a diameter of the tubular structure and/or a flow rate and/or a flow direction. These initial heat sink parameters can provide a good start for the process of determining the one or several heat sink parameters by minimizing the deviation between the measured temperature distribution and the modeled temperature distribution, which can lead to a faster determination process and to a reduced likelihood that the determination process finds a local minimum being larger than an overall minimum.

The heat sink parameter determination apparatus comprises a heat sink location providing unit for providing a heat sink location, wherein the temperature distribution measuring unit is adapted to measure the temperature distribution close to the provided heat sink location. Thus, the temperature distribution measuring unit is preferentially adapted to measure the temperature distribution adjacent to or in the vicinity of the provided heat sink location. In particular, a distance to the heat sink location may be predefined and for determining the heat sink parameter a temperature distribution can be measured in parts of the object having a distance to the heat sink location, which is equal to or smaller than the predefined distance, wherein these parts of the object may be regarded as being close to the heat sink location. If the temperature distribution is also measured in other parts of the object, preferentially only the temperature distribution measured for the close parts of the object is used for determining the heat sink parameter. The predefined distance is preferentially 3 cm, further preferred 2 cm and even further preferred 1 cm. In an embodiment the temperature distribution may be measured by using ultrasound data acquired by an ultrasound probe in one or several scan planes traversing the heat sink, especially a blood vessel, such that the one or several scan planes each comprise an intersection area where the heat sink intersects the respective scan plane. For determining the heat sink parameter only parts of the temperature distribution within the one or several scan planes may be used, which have a shortest distance to the border of the intersection area being smaller than the predefined distance, wherein these parts of the temperature distribution may be regarded as being close to the heat sink. Thus, the parts of the temperature distribution may be used only, which correspond to, for instance, a margin, especially an annulus, around the respective intersection area, wherein the thickness of the margin is defined by the predefined distance. In addition, in an embodiment from the close parts of the temperature distribution only parts may be used for determining the heat sink parameter, which have been determined based on ultrasound data which correspond to backscattered ultrasound waves which have not passed through the heat sink. Ultrasound data, which correspond to backscattered ultrasound waves which have not passed through the heat sink, are not affected by, for instance, reflections at the heat sink and can therefore have a better quality, which can lead to a higher quality temperature distribution. Since, for instance in the case of ultrasound thermometry but also when using other temperature measurement techniques, the temperature may be measurable over a limited temperature range only, during the heating process the temperature distribution measuring unit may be able to measure the temperature close to the heat sink over a relatively long time in comparison to a temperature measurement close to the heat source. More temperature data may therefore be measurable close to the heat sink and may thus be available for determining the heat sink parameter, which can lead to a further improved determination of the heat sink parameter. In an embodiment the heat sink location providing unit and the initial heat sink parameter providing unit are an integrated unit, wherein in this case the heat sink location is provided as an initial heat sink parameter.

It is preferred that the model providing unit is adapted to provide the model such that it depends also on an object parameter, wherein the parameter determination unit is adapted to determine the object parameter and the heat sink parameter by minimizing the deviation between the measured temperature distribution and the modeled temperature distribution, wherein the modeled temperature distribution is modeled based on the provided heat source parameter, the heat sink parameter to be determined and the object parameter to be determined by using the provided model. The model providing unit can be adapted to provide the model such that it depends on one or several object parameters. The object parameters may include, for instance, thermal parameters and/or electrical parameters, i.e. parameters defining thermal and/or electrical properties of the object. The thermal and electrical parameters can be, for instance, thermal and electrical conductivities especially of tissue, if the object is a person. Determining also one or several object parameters, which can be used, in addition to the determined one or several heat sink parameters, for determining the temperature distribution, can further improve the accuracy of the temperature distribution, which may be determined based on the one or several heat sink parameters and on the one or several object parameters.

In a further aspect of the present invention a temperature distribution determination apparatus for determining a temperature distribution within an object comprising a heat sink is presented, wherein the temperature distribution determination apparatus comprises:

a heat sink parameter determination apparatus for determining a parameter of the heat sink as defined herein, a temperature distribution determination unit for determining the temperature distribution within the object based on the model provided by the model providing unit, a heat source parameter provided by the heat source parameter providing unit and the determined heat sink parameter.

By using the determined heat sink parameter and the model the temperature distribution within the object can be determined, even if the temperature distribution is not measurable by the temperature distribution measuring unit, for instance, because the temperatures are outside of the temperature range measurable by the temperature distribution measuring unit.

In an embodiment the heat source is adapted to heat the object in a first heating period to a lower temperature defined by a provided first heat source parameter and in a second heating period to a higher temperature defined by a provided second heat source parameter, wherein a) the temperature distribution measuring unit is adapted to measure the temperature distribution, which is used for determining the heat sink parameter, during the first heating period, wherein the parameter determination unit is adapted to determine the heat sink parameter based on the provided model, the provided first heat source parameter and the measured temperature distribution, and b) the temperature distribution determination unit is adapted to determine, during the second heating period, the temperature distribution within the object based on the provided model, the provided second heat source parameter and the determined heat sink parameter. Moreover, it is preferred that the temperature distribution determination apparatus further comprises a temperature sensing element for sensing, in the second heating period, a temperature of the object within a temperature range in which a temperature is not measurable by the temperature distribution measuring unit, wherein the temperature distribution determination unit is adapted to determine, in the second heating period, the temperature distribution within the object based on the provided model, the provided second heat source parameter, the determined heat sink parameter and the temperature sensed by the temperature sensing element. Using the temperature measured in the second heating period by the temperature sensing element for determining the temperature distribution in the second heating period can further improve the quality of the determined temperature distribution.

Furthermore, the temperature distribution measuring unit can be adapted to measure, in the second heating period, a temperature distribution in a first spatial region, in which a temperature distribution is measurable by the temperature distribution measuring unit, wherein the temperature distribution determination unit can be adapted to determine, in the second heating period, the temperature distribution within a second spatial region, in which a temperature distribution is not measurable by the temperature distribution measuring unit, based on the provided model, the provided second heat source parameter, the determined heat sink parameter and the temperature distribution measured in the second heating period in the first spatial region. In addition to determining the heat sink parameter also an object parameter can be determined based on the provided model, the provided first heat source parameter and the temperature distribution measured during the first heating period, wherein in the second heating period the temperature distribution within the second spatial region can then be determined based on the provided model, the provided second heat source parameter, the determined heat sink parameter and the determined object parameter.

The object preferentially comprises tissue to be ablated by the heat generated by the heat source, wherein the heat sink parameter determination apparatus may further comprise an ablated region determination unit for determining a region in which tissue has been ablated.

In a further aspect of the present invention a heating system for heating an object comprising a heat sink is presented, wherein the heating system comprises:

a heat source for heating the object, and a temperature distribution determination apparatus for determining a temperature distribution within the object caused by heating the object as defined herein.

In a preferred embodiment the heating system further comprises a heating control unit for controlling the heat source depending on the determined temperature distribution. In particular, a region or interest, which should be ablated by applying heat to the region of interest, like a tumor region can be provided and compared with a determined ablated region, wherein the ablated region can be determined depending on the determined temperature distribution. The heating control unit can then be adapted to control the heating such that the determined ablated region completely covers the region of interest, in order to ensure that the region of interest has been ablated completely. In this way the heating of the object can be improved.

In another aspect of the present invention a heat sink parameter determination method for determining a parameter of a heat sink within an object is presented, wherein the heat sink parameter determination method comprises:

providing a heat sink location by a heat sink location providing unit, measuring a temperature distribution in the object close to the provided heat sink location by a temperature distribution measuring unit, providing a parameter of the heat source, which defines the heating of the object, by a heat source parameter providing unit, providing a model describing a temperature distribution in the object, while the object is heated by the heat source by a model providing unit, wherein the model depends on the heat sink parameter and the heat source parameter, determining the heat sink parameter by minimizing a deviation between the temperature distribution, which has been measured close to the provided heat sink location, and a modeled temperature distribution by a parameter determination unit, wherein the modeled temperature distribution is modeled based on the provided heat source parameter and the heat sink parameter to be determined by using the provided model.

In a further aspect of the present invention a temperature distribution determination method for determining a temperature distribution within an object comprising a heat sink is presented, wherein the temperature distribution determination method comprises:

determining a parameter of the heat sink as defined herein, determining the temperature distribution within the object based on the model provided by the model providing unit, a heat source parameter provided by the heat source parameter providing unit and the determined heat sink parameter by a temperature distribution determination unit.

In another aspect of the present invention a computer program for determining a parameter of a heat sink within an object is presented, the computer program comprising program code means for causing a heat sink parameter determination apparatus as defined herein to carry out the steps of a heat sink parameter determination method as defined herein, when the computer program is run on a computer controlling the heat sink parameter determination apparatus.

In a further aspect of the present invention a computer program for determining a temperature distribution within an object comprising a heat sink is presented, the computer program comprising program code means for causing a temperature distribution determination apparatus as defined herein to carry out the steps of a temperature distribution determination method as defined herein, when the computer program is run on a computer controlling the temperature distribution determination apparatus.

It shall be understood that the heat sink parameter determination apparatus, the temperature distribution determination apparatus, the heating system, the heat sink parameter determination method, the temperature distribution determination method, the computer program for determining a parameter of a heat sink and the computer program for determining a temperature distribution have similar and/or identical preferred embodiments, in particular, as defined and disclosed herein.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
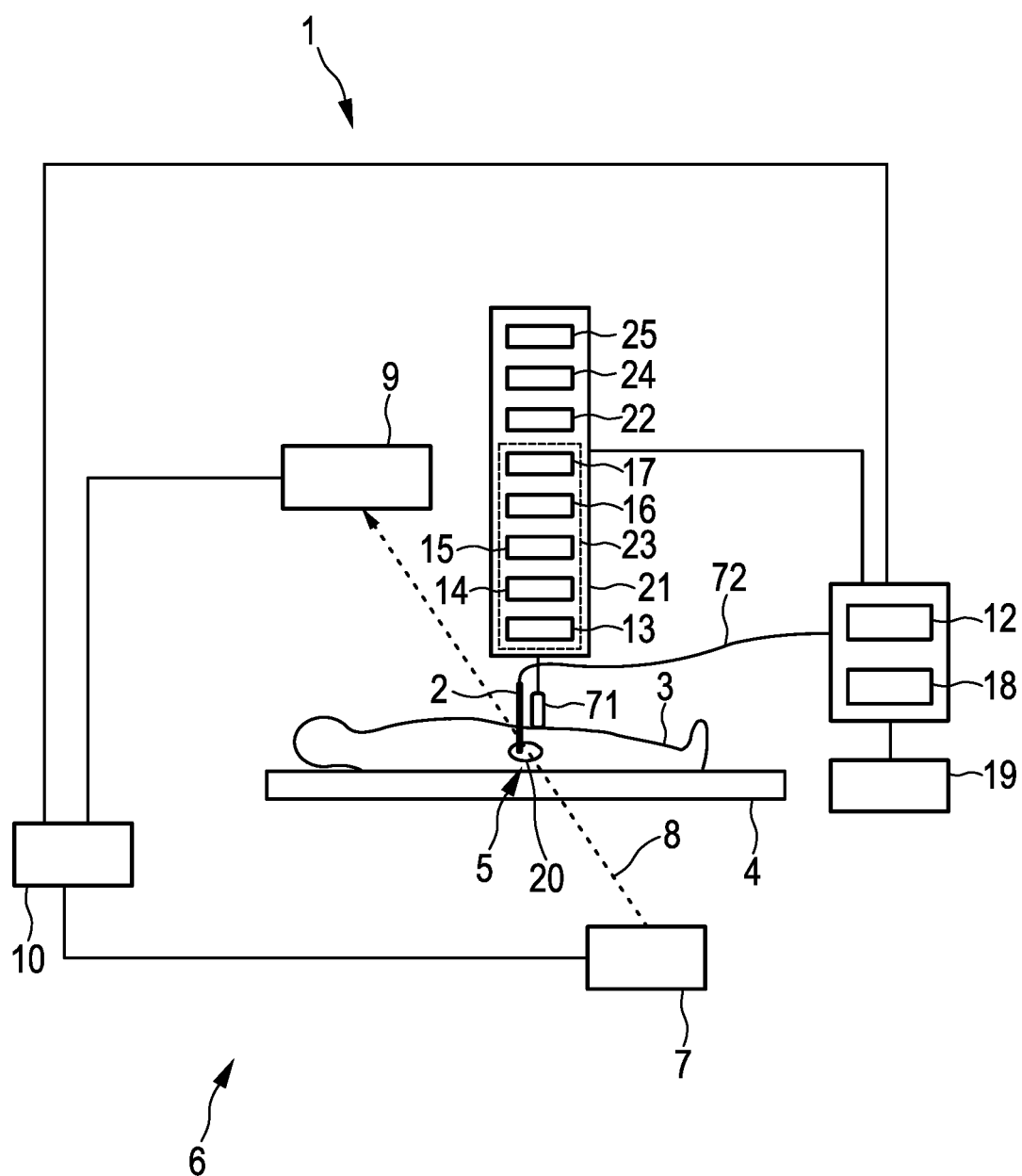
FIG. 1 shows schematically and exemplarily a heating system for heating an object comprising a heat sink.
Figure 2:
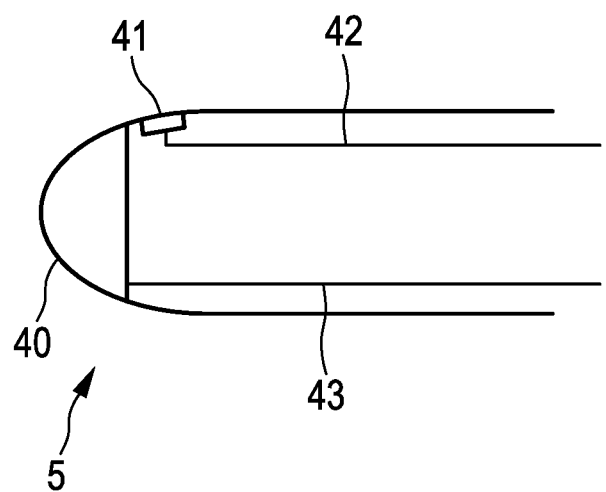
FIG. 2 shows schematically and exemplarily a tip of an ablation needle, FIGS. 3 to 6 schematically and exemplarily show mean square difference plots depending on different parameters.

FIG. 1 shows schematically and exemplarily an embodiment of a heating system for heating an object comprising a heat sink. In this embodiment the system 1 is an ablation system for ablating a tumor within a person 3 lying on a support means 4 like a patient table. The system 1 comprises a heating source 2 being an energy application element for applying energy to the person 3, in particular, to a tumor within the person 3. In this embodiment the energy application element 2 is an ablation needle comprising an ablation electrode 40 and a temperature sensing element 41 at the tip 5 of the ablation needle 2 as schematically and exemplarily illustrated in FIG. 2. The temperature sensing element 41 at the tip 5 of the ablation needle 2 is a thermocouple in this embodiment, which is electrically connected to a tip temperature measurement determining unit 18 via an electrical conductor 42 like a wire for determining the temperature at the tip 5 of the ablation needle 2 depending on electrical signals received from the thermocouple.

The energy applied to the person 3 by the ablation electrode 40 is preferentially RF energy, wherein the ablation electrode 40 is electrically connected to an ablation energy control unit 12, which may also be regarded as being a heating control unit 12 and which is adapted to control the application of the RF energy, via an electrical conductor 43 which may also be a wire. The electrical conductors 42, 43 may be arranged within the ablation needle 2 and within a cable 72 connecting the ablation needle 2 with the ablation energy control unit 12. In this embodiment the ablation energy control unit 12 comprises an RF source for providing the RF energy.

The system 1 further comprises a temperature distribution measuring unit for measuring a spatially and temporally dependent temperature distribution within the person 3, while the RF energy is applied to the person 3. The temperature distribution measuring unit comprises an ultrasound probe 71 for acquiring ultrasound data of the person 3 and an ultrasound thermometry unit 13 for determining the temperature distribution based on the acquired ultrasound data.

The system 1 further comprises a model providing unit 15 for providing a model describing a temperature distribution within the person 3, while the person 3 is heated by using the ablation needle 2, wherein the model depends on modifiable model parameters including one or several heat sink parameters, which define a cooling of the person 3 while the person 3 is heated by the ablation needle 2, and one or several heat source parameters defining the heating of the person 3 by the ablation needle 2. The modifiable parameters may further include object parameters like thermal parameters or electrical parameters of the object. In this embodiment a tumor in the liver 20 of the person 3 should be ablated such that the modifiable model parameters may include the thermal conductivity and the electrical conductivity of the liver 20.

The heat sinks are blood vessels within the liver 20. The heat sink parameters include, for example, the location of the respective blood vessel, the diameter of the respective blood vessel, the flow rate through the respective blood vessel, the direction of flow through the respective blood vessel, et cetera. The heat source parameters include, for instance, the location of the ablation needle within the person 3, the times at which energy is applied to the person 3, the amount of energy applied to the person 3, et cetera. The heat source parameters can be provided by a heat source parameter providing unit 14, which may have received information about the times, at which the energy is applied, and about the amount of the applied energy from the ablation energy control unit 12. In particular, there can be a continuous data stream from the ablation energy control unit 12 to the heat source parameter providing unit 14, in order to send this information from the ablation control unit 12 to the heat source parameter providing unit 14. The information about the location of the ablation needle 2 within the person 3 may be provided to the heat source parameter providing unit 14 by a localization system 6, which will be described in more detail further below.

The system 1 further comprises a parameter determination unit 16 for determining the heat sink parameters by minimizing a deviation between the measured temperature distribution and a modeled temperature distribution, wherein the modeled temperature distribution is modeled based on the provided heat source parameters and the heat sink parameters to be determined by using the provided model. The parameter determination unit 16 may further consider object parameters like the thermal and electrical conductivities of the liver tissue during the modeling step, thereby also determining these object parameters. The parameter determination unit 16 can be adapted to additionally use the temperature measured by the temperature sensing element (e.g., thermocouple) 41 at the tip 5 of the ablation needle 2, wherein in this case the modeled temperature distribution is modeled such that a deviation between a) the measured temperature distribution, which is measured by the temperature distribution measuring unit 13 (in connection with ultrasound probe 71), and the temperature measured by the temperature sensing element 41 at the tip 5 of the ablation needle 2 and b) the modeled temperature distribution is minimized.

The localization system 6 is adapted to detect the position of the tip 5 of the ablation needle 2 within the person 3. In this embodiment the localization system 6 is an x-ray fluoroscopy system, in particular, an x-ray C-arm system. The x-ray fluoroscopy system comprises an x-ray source 7 for generating x-rays 8 which traverse the person 3 on the support means 4, wherein the x-rays 8, which have traversed the person 3, are detected by an x-ray detector 9. The x-ray fluoroscopy system 6 further comprises a fluoroscopy control unit 10 for controlling the x-ray source 7 and the x-ray detector 9. The x-ray detector 9 generates x-ray images of the person 3, which can be shown on a display 19 and which can be used to determine the position of the tip 5 of the ablation needle 2.

The x-ray fluoroscopy system is preferentially an x-ray C-arm system, which allows acquiring x-ray projection images in different acquisition directions, wherein the fluoroscopy control unit 10 may be adapted to reconstruct a computed tomography (CT) image from the x-ray projection images acquired in different acquisition directions. In the CT image the tip 5 of the ablation needle 2 may be segmented, in order to determine its position.

The system 1 preferentially further comprises a heat sink location providing unit 17 for providing a heat sink location based on the reconstructed CT image, wherein the temperature distribution measuring unit 13, 71 can be adapted to measure the temperature distribution, which is used for determining the heat sink parameters, close to the provided heat sink location. For instance, the heat sink location providing unit 17 can be adapted to segment blood vessels within the liver 20 in the reconstructed CT image, in order to provide the locations of the blood vessels. These locations of the blood vessels can also be used as initial heat sink parameters, which can be used to initialize the model before the parameter determination unit 16 determines the heat sink parameters such that the process of determining the heat sink parameters is started with the initialized model. The heat sink location providing unit 17 can therefore also be regarded as being an initial heat sink parameter providing unit. In other embodiments the heat sink location providing unit 17 can be adapted to determine the heat sink locations in another way, for instance, based on other images like a CT image generated by a CT system, a magnetic resonance (MR) image generated by an MR imaging system, an ultrasound image generated by an ultrasound probe, especially by the ultrasound probe already used for the ultrasound thermometry, et cetera.

The ultrasound probe 71 may be adapted to measure the ultrasound data for one or several scan planes, wherein the heat source parameter providing unit 14 may be adapted to provide the location of the ablation needle 2 relative to the location of the one or several scan planes. For instance, the CT image can be used to determine the location of the ablation needle relative to the one or several scan planes by segmenting the ablation needle 2 and the ultrasound probe 71 in the CT image and by using a known spatial relationship between the ultrasound probe 71 and the one or several scan planes. This known spatial relationship can be provided by the ultrasound probe 71. Also other images can be used for determining the location of the ablation needle 2 relative to the location of the one or several scan planes like ultrasound images which may be generated by using the ultrasound probe 71 or by using another ultrasound probe.

In other embodiments other localization techniques for detecting the position of the needle tip within the person can be used like localization techniques which are based on EM sensors, OSS sensors, et cetera.

The temperature distribution measuring unit 13 (in connection with ultrasound probe 71), the heat source parameter providing unit 14, the model providing unit 15, the parameter determination unit 16 and the heat sink parameter providing unit 17 are used for determining one or several heat sink parameters, i.e. in this embodiment parameters of blood vessels, within the person 3. These units can therefore be regarded as forming a heat sink parameter determination apparatus for determining parameters of heat sinks within the person 3.

The system 1 further comprises a temperature distribution determination unit 22 for determining a temperature distribution within the person 3 based on the provided model, a heat source parameter provided by the heat source parameter providing unit 14 and the determined heat sink parameters. In particular, the ablation needle 2 is preferentially used to heat the person 3 in a first heating period to a lower temperature defined by first heat source parameters provided by the heat source parameter providing unit 14 and in a second heating period to a higher temperature defined by second heat source parameters provided by the heat source parameter providing unit 14. In the second heating period the temperature is high enough to ablate the tumor region within the liver 20. The temperature distribution measuring unit 13 (in connection with ultrasound probe 71) is preferentially used to measure the temperature distribution, which is used for determining the heat sink parameters, during the first heating period, wherein the parameter determination unit 16 determines the heat sink parameters based on the provided model, the provided first heat source parameters and the measured temperature distribution. Moreover, the temperature distribution determination unit 22 preferentially determines, during the second heating period, the temperature distribution within the person 3 based on the provided model, the provided second heat source parameters and the determined heat sink parameters. Moreover, the temperature distribution measuring unit 13 (in connection with ultrasound probe 71) may be adapted to measure, in the second heating period, a temperature distribution in a first spatial region, in which a temperature distribution is measurable by the temperature distribution measuring unit 13 (in connection with ultrasound probe 71), wherein the temperature distribution determination unit 22 may be adapted to determine, in the second heating period, the temperature distribution within a second spatial region, in which the temperature distribution is not measurable by the temperature distribution measuring unit 13 (in connection with ultrasound probe 71), based on the provided model, the provided second heat source parameters, the determined heat sink parameters and the temperature distribution measured in the second heating period in the first spatial region. For instance, the second spatial region may be a region close to the location of the ablation needle 2. Since in this example the second spatial region is close to the location of the ablation needle 2, the temperatures within the second spatial region will be relatively high, especially higher than 50 degrees Celsius, and therefore not be measurable by ultrasound thermometry. The first spatial region has preferentially a distance to the ablation needle 2, which is large enough to have temperatures within a temperature range, which is measurable by ultrasound thermometry. The temperature distribution in the second spatial region can then be determined by using the provided model, the provided second heat source parameters, the determined heat sink parameters and the temperature distribution measured in the first spatial region by adapting the model with the determined heat sink parameters such that a deviation between the temperature distribution measured in the first spatial region and the modeled temperature distribution in the first spatial region is minimized. The temperature distribution provided by the adapted model in the second spatial region is then regarded as being the temperature distribution in this second spatial region. Thus, a temperature distribution can be provided in the second spatial region, although the temperature distribution cannot directly be measured in the second spatial region. The modeling of the temperature distribution can further consider object parameters like thermal and electrical tissue conductivities, which may have been determined based on the temperature measurements performed during the first heating period. Moreover, the modeling can consider temperatures measured during the second heating period by the temperature sensing element (e.g., thermocouple) 41 at the tip 5 of the ablation needle 2, wherein in this case the modeling can be performed such that a deviation between a) the temperature distribution measured in the first spatial region and the temperatures measured by the temperature sensing element 41 and b) the modeled temperature distribution in the first spatial region and at the position of the temperature sensing element 41 is minimized.

The first heating period is preferentially a heating period, in which the tissue of the person 3 is heated to a temperature, which is measurable by ultrasound thermometry, wherein in this low temperature phase heat sink parameters and optionally also object parameters like thermal and electrical conductivities are determined. During the second heating period the tissue of the person 3 is preferentially heated to temperatures, which can be used to ablate regions of the tissue, in particular, a tumor region, wherein in this case the temperature distribution close to the ablation needle can be modeled as described above.

The first spatial region has preferentially a distance to the tip 5 of the ablation needle 2 such that the temperature in the first spatial region will be smaller than about 50 degrees Celsius, if the ablation energy is applied to the person 3 in the second heating period. This ensures that the temperature distribution measuring unit 13 (in connection with ultrasound probe 71) can measure the temperature distribution also during the ablation procedure in the first spatial region. The second spatial region is closer to the tip 5 of the ablation needle 2. Preferentially, the second spatial region is adjacent to the tip 5 of the ablation needle 2 and covers a region of interest to be ablated and a surrounding region surrounding the region of interest. In this example the region of interest is a tumor region within the liver 20. Thus, the heat sink parameter determination apparatus 23 (in connection with ultrasound probe 71) and the temperature distribution determination unit 22 are preferentially adapted such that a temperature distribution can be estimated in the tumor region and in a surrounding region around the tumor region, wherein these regions may define the second spatial region. The second spatial region can also be a larger region, which also covers further regions, which are further away from the tip 5 of the ablation needle 2 and in which the tissue is also heated to a temperature higher than 50 degrees Celsius.

The heat sink parameter determination unit 23 (in connection with ultrasound probe 71) and the temperature distribution determination unit 22 are part of a temperature distribution determination apparatus 21 (in connection with ultrasound probe 71), for determining a temperature distribution within the person 3, especially for determining an overall temperature distribution within the first and second spatial regions.

The temperature distribution determination apparatus further comprises an ablated region determination unit 24 for determining an ablated region defining a region within the person 3 that has been ablated, wherein the ablated region determination unit 24 is adapted to determine the ablated region by determining a part of the person 3 for which the estimated temperature distribution in the second spatial region comprises or has comprised a temperature being higher than a predefined temperature threshold. The temperature distribution determination apparatus 21 (in connection with ultrasound probe 71), also comprises a region of interest providing unit 25 for providing the region of interest being, in this embodiment, a tumor region, which should be ablated, wherein the determined ablated region and the tumor region can be shown on the display 19. For instance, an overlay of the determined ablated region and the tumor region can be shown on the display 19. The predefined temperature threshold is, for instance, 60, 65 or 70 degrees Celsius.

The ablation energy control unit 12 can be adapted to control the ablation needle 2, i.e. the power of the ablation, depending on the determined temperature distribution. In particular, the ablation energy control unit 12 can be adapted to control the ablation power such that the tumor region is completely ablated.

In another embodiment the modeling may consider temperatures measured during the second heating period by the thermocouple 41 at the tip 5 of the ablation needle 2, without considering a thermometry measurement, wherein in this case the modeling can be performed such that a deviation between a) the temperatures measured by the thermocouple 41 and b) the modeled temperature distribution at the position of the thermocouple 41 is minimized. In particular, in an embodiment the only temperature measurement being input in the modeling during the second heating period may be the temperature measurement of the thermocouple 41. Also in this case the ablated region determination unit 24 can be used to determine an ablated region based on the determined temperature distribution.

In this embodiment the ablation needle 2 is navigated directly by hand. In another embodiment the system can further comprise a navigation unit for navigating the ablation needle, in particular the needle tip, to a desired location within the person. The navigation unit can be adapted to allow a user to navigate the ablation needle completely by hand or semi-automatically. The ablation needle may comprise built-in guiding means, which can be controlled by the navigation unit. The ablation needle can, for example, be steered and navigated by the use of steering wires, in order to guide the needle tip to a desired location within the person.

Thermal ablation techniques are excellent alternatives to major surgery, which can pose a risk even with the most experienced surgeon. These techniques are minimally invasive requiring only needles, which may be adapted to perform an RF therapy, a cryotherapy or a microwave ablation therapy, or they are non-invasive, wherein, for instance, a non-invasive heat source such as an ultrasound heating source like a high intensity focused ultrasound (HIFU) source is used. In most of the procedures, cancerous tissue is heated to temperatures above 60 degrees Celsius and coagulated.

For performing an RF ablation (RFA) procedure the system described above with reference to FIG. 1 comprises a probe with an active electrode tip, i.e. the ablation needle, through which preferentially a 460 to 500 kHz alternating current is conducted. The current propagates through the body of the person 3 to grounding pads (not shown in FIG. 1 for clarity reasons) placed either on the back or the thigh of the person 3. The current causes ionic agitation and frictional heating. Heat is then dissipated through thermal conduction to ablate the tumor region. In this embodiment RFA is used to treat liver cancer.

In the embodiment described above with reference to FIG. 1 RFA is performed under x-ray guidance by using an x-ray C-arm system. However, the RFA can also be performed by using another guidance system, which may be based on ultrasound imaging, CT imaging or MR imaging guidance. A follow-up examination is preferentially done by using a CT scan or MRI scan within, for example, a month to assess effectiveness of ablation and again at three months intervals along with tumor markers to detect residual disease or recurrence. After state of the art ablation procedures have been performed, relatively high recurrence rates are often observed because of the often present inability to monitor and control ablation size sufficiently to adequately kill the tumor cells. The system described above with reference to FIG. 1 provides therefore real-time feedback to the clinician by providing a temperature map of the ablated zone. This could also be achieved with reasonable accuracy with MR based temperature imaging. However, MR imaging is expensive and may not be readily available. Ultrasound is another modality that may be used for image guidance during placement of the needle. Due to its ease of use and availability it may be a preferred method for monitoring the lesions. However, in the prior art ultrasound is used generally for monitoring the treatment by visualizing the hyperechoic lesions on a B-mode image. Such visualization is only approximate and not a good indicator of the treatment efficacy.

The system described above with reference to FIG. 1 uses an ultrasound probe 71 and an ultrasound thermometry unit 13 for performing three-dimensional ultrasound thermometry. The ultrasound probe 71 and the ultrasound thermometry unit 13 are preferentially adapted to measure the three-dimensional spatial and temporal temperature distribution as described, for instance, in the article "Three-dimensional spatial and temporal temperature imaging in gel phantoms using backscattered ultrasound" by A. Anand et al., IEEE Transactions on Ultrasonics, Ferroelectrics and Frequency Control, 54(1), pages 23 to 31 (2007), which is herewith incorporated by reference.

The underlying principle of ultrasound thermometry is that the speed of sound in tissue changes as a function of temperature which manifests as apparent shifts, i.e. displacements, in ultrasound echoes. The resulting "temperature-induced strain", which is mathematically derived by differentiating the displacement along the ultrasound beam direction, is nominally proportional to the temperature rise in the range up to 50 degrees Celsius. However, the problem lies in the variation in trend of the temperature dependence of speed of sound for various tissues. For example, for liver tissues the speed of sound increases approximately linearly with temperature up to a temperature range of 50 degrees Celsius, after which the trend plateaus. Hence, there is no sensitivity to ultrasound echo shifts with temperatures beyond this temperature range. Also, with the onset of tissue necrosis and the resulting changes in tissue structure, the signature of the ultrasound echoes changes significantly and makes the comparison of ultrasound echoes to determine the displacement difficult. Therefore, for temperatures above 50 degrees Celsius the ultrasound thermometry, which is based on tracking changes in speed of sound, is not a reliable indicator of temperature in the tissue.

In the first heating period the tissue is therefore preferentially heated up to 50 degrees Celsius only, at least in the spatial regions where the ultrasound data for determining the temperature distribution are measured, wherein these ultrasound data are preferentially measured in a plane close to a blood vessel. The close plane may be parallel to the blood vessel or traverse the blood vessel. Moreover, during the second heating period the first spatial region, in which ultrasound data may be measured, is preferentially chosen such that the temperature is not higher than 50 degrees Celsius within the first spatial region.

Organs such as the liver, to which cancer-related ablative therapies are often applied, are highly vascularized, wherein blood vessels, especially blood vessels having a diameter being larger than 3 mm, impact the efficacy of ablative treatments such as RF ablation. Ablation planning and ablation monitoring can therefore be improved, if the effects of these blood vessels are considered. Thus, the system described above with reference to FIG. 1 characterizes their heat sink effect and determines how it will affect the surrounding tissue and may result in incomplete ablations. This information may also be used to adapt therapy delivery parameters, before the entire ablation procedure has been completed. For instance, before the ablation is performed in the second heating period, in the first heating period the heat sink parameters being indicative of the heat sink effect can be determined, wherein these heat sink parameters can be used to determine the temperature distribution also close to the ablation needle during the second heating period, in which the tumor region should be ablated, wherein during the ablation procedure heat source parameters like the thermal dose applied to the tissue can be modified in real-time based on a currently estimated temperature distribution close to the ablation needle.

The system described above with reference to FIG. 1 is preferentially adapted to determine heat sink parameters defining, for instance, the morphology, i.e. geometric parameters such as position and size, of heat sinks in the vicinity of an ablative heat source, in order to determine its potential detrimental effect on the therapy efficacy. The system is preferentially adapted to acquire ultrasound data in the vicinity of the respective heat sink during a low power heating exercise, i.e. during the first heating period, where after the ultrasound data are coupled to the thermal model that includes the ability to model heat sinks to estimate model parameters including at least heat sink parameters. The thermal model is then preferentially used to infer temperatures over the entire volume including the core of the heating zone. Finally, an estimated temperature map, i.e. a temporal and spatial temperature distribution, is preferentially provided to a physician and the extent of the ablation zone is preferentially determined based on the estimated temperature map.

The system described above with reference to FIG. 1 is preferentially configured to adapt the thermal model, which preferentially simulates ablation heating in the presence of blood vessels, with real-time temperature measurements obtained by using ultrasound thermometry. Preferentially, the temperature distribution over the entire ablation zone is estimated and an undertreatment caused by the presence of blood vessels is extracted. The system preferentially solves the following problems of the prior art.

The extent of an ablated region may be determined more accurately. Moreover, in the prior art ultrasound B-mode inspection guided by hyperechoic visualization of the ablated region is often not accurate, which may render difficult to assess the effectiveness of therapy. The hyperechoes visualized on B-mode images are caused by gas and vapor bubbles. In order to generate these bubbles and visualize the treatment region on ultrasound, an ablation treatment protocol involves heating to temperatures in the order of 100 degrees Celsius which is overkill for achieving necrosis that only requires temperatures up to 70 to 80 degrees Celsius. Hence, if ultrasound B-mode imaging is used for visually monitoring the ablation procedure, the treatment time is longer than it needs to be. Furthermore, known non-invasive methods do not perform a functional evaluation of the impact of cooling by blood vessels. While, for instance, CT or ultrasound Doppler images can provide anatomical information in terms of the location and size of the blood vessels and the velocities of the blood flowing through the blood vessels, the thermal impact of these structures is not determined and considered by these known non-invasive methods. In contrast, the system described above with reference to FIG. 1 evaluates the functional impact of cooling by blood vessels and considers this functional impact while determining the temperature distribution during the ablation process, i.e. during the second heating period. The effectiveness of readily available ultrasound data can therefore be improved during RF ablation treatments and an instant feedback on the treatment can be provided.

The system described above with reference to FIG. 1 is adapted to utilize ultrasound thermometry and estimate the temperature distribution over the entire volume in the presence of heat sinks such as blood vessels. The system comprises an ultrasound acquisition system, i.e. the temperature distribution measuring unit, that provides thermometry estimates preferentially during a low power heating pulse, i.e. during the first heating period, immediately before the start of the ablation procedure, i.e. immediately before the second heating period. The ultrasound data are preferentially acquired in one or several scan planes, wherein two-dimensional ultrasound transducer matrix arrays may be used, around the heat source being, in this embodiment, the ablation needle 2. Preferably, the one or several scan planes are located close to the blood vessels so that their cooling effect can be optimally captured. They may be parallel to the blood vessel or traverse the blood vessel. A thermal model is provided, which can be a multiphysics model and which is configured to simulate the energy deposition in tissue based on the used modality which in this embodiment is an RF ablation needle, but which may also be another heat source like a microwave heat source or a HIFU heat source. The model is further configured to simulate thermal diffusion resulting from the heat generation by the heat source and the heat transfer in fluids like blood. Tissue specific properties such as thermal and electrical parameters and parameters of the heat sinks like their positions, diameter, et cetera, are preferentially assumed as unknown parameters and are preferentially estimated in situ using the ultrasound thermometry data measured by the temperature distribution measuring unit. Optionally, if anatomical information is available from pre-acquired imaging data, this information may be used to initialize the locations of the blood vessels in the model and, if available from, for instance, ultrasound Doppler data, the flow direction may be initialized in the model. The anatomical information may also be used to position the ultrasound scan planes for performing the thermometry close to the blood vessels, wherein the scan planes may be parallel to the blood vessel or traverse the blood vessel. The parameter determination unit, which may also be regarded as being an analysis module, is adapted to estimate then the relevant blood vessel parameters like the position, diameter, flow rate, et cetera, and preferentially to also estimate tissue parameters like electrical and thermal parameters. Finally, these parameters may be used to determine a volumetric temperature distribution optionally along with the applied thermal dose and/or a lesion size by using the model.

The system described above with reference to FIG. 1 is adapted to estimate the relevant parameters in the thermal model that characterize the heat sinks, i.e. in this embodiment the heat sink parameters characterizing the blood vessels, in the presence of an ablation heat source, which is the ablation needle in this embodiment. Once the heat sink parameters and optionally further parameters like tissue parameters have been estimated in the thermal model, the volumetric temperature distribution can be estimated by a forward simulation.

The thermal model is preferentially a finite element method (FEM) model, which may be developed by using the software COMSOL Multiphysics from the company COMSOL, Inc. The thermal model simulates the heating caused by the power applied to the ablation electrode at the tip 5 of the ablation needle, wherein the thermal model preferentially uses following equations:

$$\nabla \cdot [\sigma \nabla V] = 0 \qquad (1)$$

$$\rho C \frac{dT}{dt} = \nabla \cdot (k \nabla T) + \sigma |\nabla V|^2 \quad \text{and} \qquad (2)$$

$$\rho_f C_f \left(\frac{dT}{dt}\right) + \rho_f C_f v \cdot \nabla T = \nabla \cdot (k_f \nabla T) + \sigma_f |\nabla V|^2. \qquad (3)$$

In these equations V denotes the electrical potential distribution, T denotes the temperature distribution, σ denotes the electrical conductivity, ρ denotes the density, C denotes the specific heat, t denotes the time, k denotes the thermal conductivity and v denotes the flow velocity in a blood vessel. The variables without subscripts represent variables of tissue and the variables with the subscript f represent fluid variables. The density ρ and the specific heat C are preferentially assumed to be known and may be based on typical values known from literature. The thermal conductivity k and the electrical conductivity σ are preferentially considered as unknown. Moreover, the heat sink parameters like the locations and diameters of the blood vessels and the flow rates of the blood flowing through the blood vessels are also considered as being unknown. These unknown parameters are determined by the parameter determination unit from a comparison between the model and measured ultrasound thermometry data. In an embodiment it is assumed that the electrical conductivity σ is independent of the temperature such that equation (1) becomes:

$$(\sigma \nabla^2 V) = 0 \qquad (4)$$

The simulation may consider two different kinds of spatial regions like blood regions and tissue regions, wherein parameters like the thermal conductivity, the density, the specific heat and the electrical conductivity may be different in the two different kinds of spatial regions. However, in an embodiment the simulation may also consider more different kinds of spatial regions. Moreover, the simulation may consider a tissue property distribution and a corresponding distribution of tissue parameters as a function of space.

The parameter determination unit can be adapted to run the thermal model for different combinations of the unknown parameters, i.e. of the heat sink parameters and optionally also of object parameters like electrical and thermal tissue parameters. For the electrical conductivity σ a unity value may be used during the simulation with the different combinations, because the electrical conductivity σ just linearly affects the temperature distribution as can be seen in above equation (2) and it can be estimated by a simple scaling operation. For each combination of parameters a temperature distribution can be modeled and stored in a memory for the respective ultrasound scan plane. The sweep range for the unknown parameters is preferentially chosen to be physically meaningful. In order to determine the best combination of parameters, the parameter determination unit can compare the experimental data, i.e. the measured temperature distributions, with the stored modeled temperature distribution and perform a linear fit to estimate the unknown parameter σ. The comparison can be based on a similarity measure like a mean square difference (MSD). The parameter determination unit can be adapted to determine the combination of parameters providing the largest similarity between the respective modeled temperature distribution and the measured temperature distribution.

Figure 3:
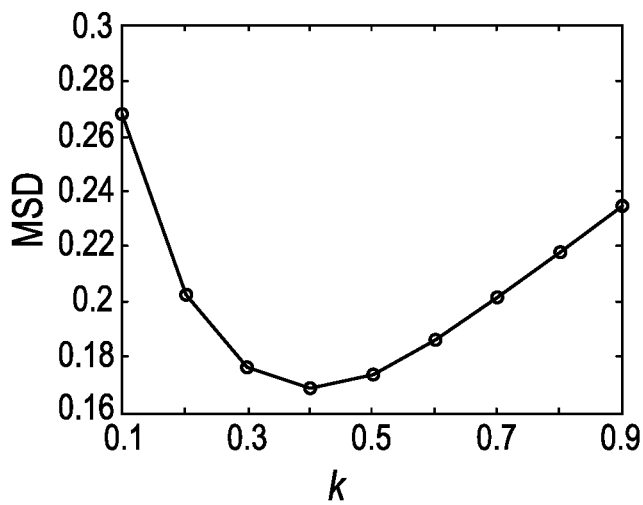
Figure 4:
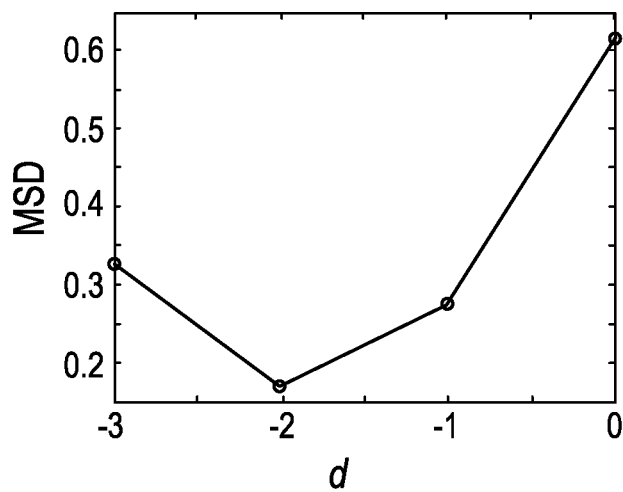
Figure 5:
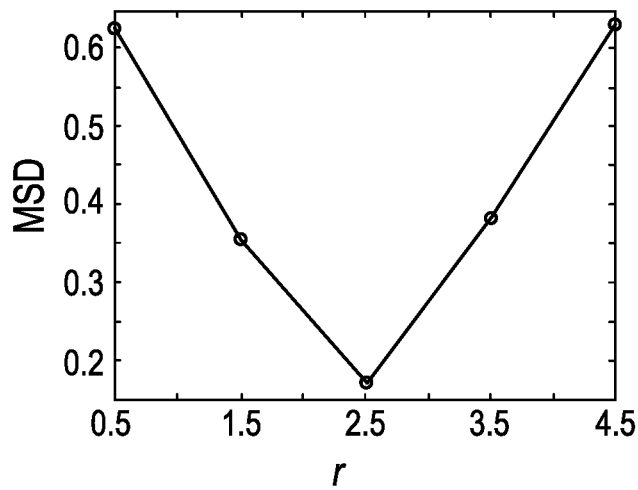
Figure 6:
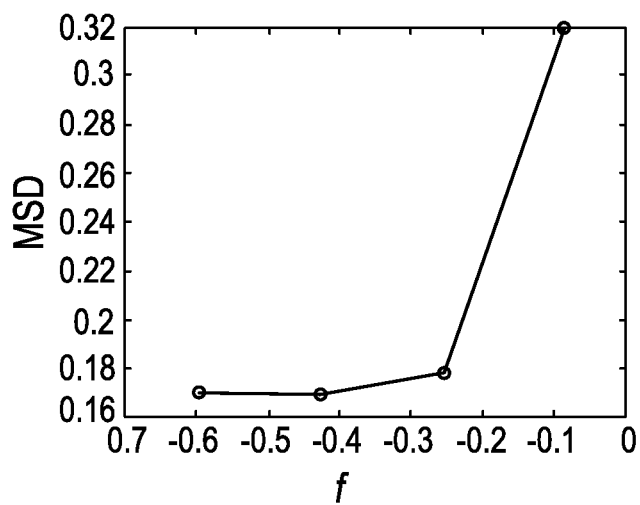
Figure 7:
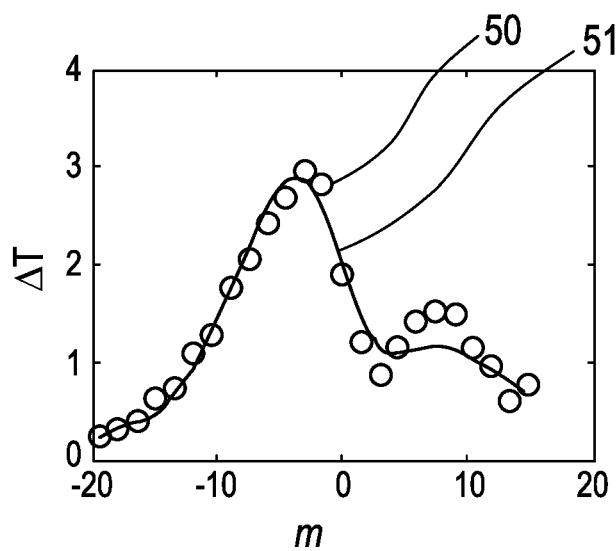
FIG. 7 illustrates measured temperatures and modeled temperatures.

FIGS. 3 to 6 schematically and exemplarily show one-dimensional MSD plots for a respective parameter, wherein the respective other parameters are constant and have values leading to a respective smallest MSD. In particular, FIG. 3 shows schematically and exemplarily the MSD depending on the thermal conductivity k, FIG. 4 shows schematically and exemplarily the MSD depending on a dimension d of the location of a blood vessel, FIG. 5 schematically and exemplarily shows the MSD depending on the radius r of the blood vessel and FIG. 6 schematically and exemplarily shows the MSD depending on a flow rate f of a flow of blood through the blood vessel, wherein in each of these plots the parameters are shown in arbitrary units. FIG. 7 shows schematically and exemplarily a temperature rise ΔT along a spatial line along which temperatures have been measured by ultrasound thermometry. The different positions along the spatial line are indicated by m, the circles 50 indicate the measured temperatures and the curve 51 represents a temperature rise as defined by the thermal model with the determined parameters. As can be seen in FIG. 7, the thermal model with the determined parameters very well fits the measured temperatures. After the parameter determination unit has determined these parameters, the temperature distribution determination unit can use these parameters together with the thermal model, in order to determine a volumetric temperature distribution.

Figure 8:
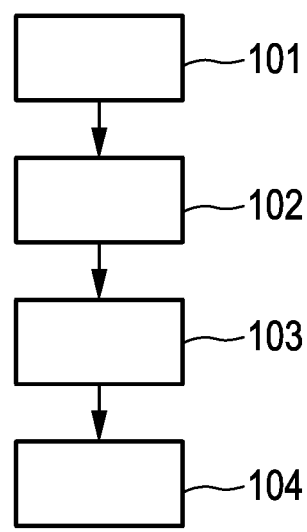
FIG. 8 shows a flowchart exemplarily illustrating an embodiment of a temperature distribution method for determining a temperature distribution within the object.

In the following an embodiment of a temperature distribution determination method for determining a temperature distribution within an object comprising a heat sink will exemplarily be described with reference to a flowchart shown in FIG. 8.

After the heat source has been placed within the object, in a first heating period, step 101, the object is heated to a relatively low temperature by the heat source, while a temperature distribution is measured by the temperature distribution measuring unit. In particular, the heat source is an ablation element placed within a liver tumor to be ablated, wherein the ablation element is used to heat the liver tumor to a relatively low temperature, which is preferentially smaller than 50 degrees Celsius, while the temperature distribution is preferentially measured by ultrasound thermometry.

In step 102, parameters of the heat source, which define the heating of the object, are provided by the heat source parameter providing unit, and a thermal model describing a temperature distribution in the object, while the object is heated by the heat source, is provided by the model providing unit, wherein the model depends on heat sink parameter and the heat source parameters. Preferentially, the heat sink parameters include the location of a blood vessel, the diameter of a blood vessel, the blood flow direction and the blood flow rate. The heat source parameters include preferentially the times at which the liver tumor is heated, the amount of heat applied to the liver tumor and the location of the heat source.

In step 103, the heat sink parameters are determined by minimizing a deviation between the measured temperature distribution and a modeled temperature distribution by the parameter determination unit, wherein the modeled temperature distribution is modeled based on the provided heat source parameters and the heat sink parameters to be determined by using the provided model. Steps 101 to 103 can be regarded as being steps of a heat sink parameter determination method for determining a parameter of a heat sink within an object.

In step 104, a second heating period, the object is heated to a higher temperature and the temperature distribution within the object is determined based on the model provided by the model providing unit, a heat source parameter defining the heating during the second heating period provided by the heat source parameter providing unit and the determined heat sink parameters by the temperature distribution determination unit. In particular, in step 104, an ablation procedure is performed, wherein during the ablation procedure the temperature distribution is determined by using the model with the determined heat sink parameters, in order to monitor the ablation process.

Although in above described embodiments an ultrasound probe measures ultrasound data in one or several scan planes, in order measure a temperature distribution by thermometry, in another embodiment the ultrasound probe may be adapted to measure the ultrasound data in three dimensions, in order to measure a three-dimensional temperature distribution by thermometry.

Although in above described embodiments the ablation element comprises a single ablation electrode, in other embodiments the ablation element can also comprise more ablation electrodes. Moreover, although in above described embodiments the ablation element comprises a single temperature sensing element, i.e. in the described embodiments a single thermocouple, in other embodiments the ablation element can also comprise several temperature sensing elements or no temperature sensing element.

Although in above described embodiments the ablation element is an RF ablation element, in other embodiments other ablation elements may be used for ablating tissue like HIFU ablation elements, microwave ablation elements or laser ablation elements.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the heat sink parameters, the determination of the temperature distributions, the provision of the model, et cetera performed by one or several units or devices can be performed by any other number of units or devices. These procedures and/or the control of the temperature distribution determination apparatus in accordance with the temperature distribution determination method and/or the control of the heat sink parameter determination apparatus in accordance with the heat sink parameter determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a heat sink parameter determination apparatus for determining a parameter of a heat sink like a blood vessel within an object such as a person by minimizing a deviation between a measured temperature distribution, which has preferentially been measured by ultrasound thermometry, and a modeled temperature distribution, wherein the modeled temperature distribution is modeled based on a provided heat source parameter like the location of an ablation needle and the heat sink parameter to be determined by using a given thermal model. This determination of heat sink parameters, which may be geometric and/or flow parameters, considers the real temperature distribution and is thus based on real heat sink influences on the temperature distribution. This can lead to an improved determination of heat sink parameters and hence to a more accurate temperature distribution which may be determined based on the determined heat sink parameters.

The invention claimed is:

1. A heat sink parameter determination apparatus for determining a desired heat sink parameter of a heat sink within an object, the heat sink parameter determination apparatus comprising:
a heat source parameter providing unit for providing a heat source parameter of a heat source, which defines a heating of the object,
a model providing unit for providing a model describing a first temperature distribution in the object, while the object is heated by the heat source, wherein the model depends on (i) one or several heat sink parameters of the heat sink, other than the desired heat sink parameter, which define a cooling of the object while the object is heated, and (ii) the heat source parameter, characterized by
a heat sink location providing unit for providing a heat sink location,
a temperature distribution measuring unit for measuring a second temperature distribution in the object close to the heat sink location but not at the heat sink location itself, wherein close to the heat sink location includes only parts of the object having a distance to the heat sink location which is equal to or smaller than a predefined distance from the heat sink location, but not at the heat sink location itself, wherein the predefined distance is selected from the group consisting of 3 cm, 2 cm, and 1 cm, and
a parameter determination unit for determining the desired heat sink parameter by minimizing a deviation between (i) the second temperature distribution, which has been measured close to the heat sink location which includes only parts of the object having the distance to the heat sink location which is equal to or smaller than the predefined distance from the heat sink location, but not at the heat sink location itself, and (ii) the first temperature distribution that comprises a modeled temperature distribution, wherein the modeled temperature distribution is modeled, via the model provided by the model providing unit, based on (a) the provided heat source parameter and (b) the one or several heat sink parameters, other than the desired heat sink parameter.

2. The heat sink parameter determination apparatus as defined in claim 1, wherein the heat sink parameter determination apparatus is adapted to determine the desired heat sink parameter selected from the group consisting of parameters which include a different heat sink location within the object, different from the heat sink location provided via the heat sink providing unit, and/or, if the heat sink includes a tubular structure with a flowing fluid, a flow direction and/or a radius of the tubular structure and/or a flow rate.

3. The heat sink parameter determination apparatus as defined in claim 1, further comprising:
an initial heat sink parameter providing unit for providing an initial heat sink parameter for initializing the model, and
wherein the parameter determination unit is further adapted to start a determination of the desired heat sink parameter with the model initialized via the initial heat sink parameter.

4. The heat sink parameter determination apparatus as defined in claim 1, wherein the model providing unit is further adapted for providing the model describing the first temperature distribution such that the model depends also on an object parameter and wherein the parameter determination unit is further adapted to determine the object parameter and the desired heat sink parameter by minimizing a deviation between (i) the second temperature distribution and (ii) the modeled temperature distribution, wherein the modeled temperature distribution is modeled based on the heat source parameter, the one or several heat sink parameters and the object parameter to be determined by using the provided model.

5. The heat sink parameter determination apparatus as defined in claim 1, wherein the temperature distribution measuring unit comprises an ultrasound probe for acquiring ultrasound data of the object and an ultrasound thermometry unit for determining a temperature distribution based on the ultrasound data that corresponds to the second temperature distribution.

6. The heat sink parameter determination apparatus as defined in claim 5, wherein the heat sink location providing unit is adapted to determine the heat sink location based on ultrasound data of the object acquired by the ultrasound probe.

7. A temperature distribution determination apparatus including the heat sink parameter determination apparatus as defined in claim 1, the temperature distribution determining apparatus for determining the first and second temperature distribution within the object that includes the heat sink, wherein the temperature distribution determination apparatus comprises:
a temperature distribution determination unit for determining the first temperature distribution within the object based on the model provided by the model providing unit, the heat source parameter, and the desired heat sink parameter.

8. The temperature distribution determination apparatus as defined in claim 7, wherein the heat source is adapted to heat the object in a first heating period to a lower temperature defined by a provided first heat source parameter and in a second heating period to a higher temperature defined by a provided second heat source parameter, wherein
the temperature distribution measuring unit is adapted to measure the first temperature distribution, which is used for determining the desired heat sink parameter, during the first heating period, wherein the parameter determination unit is adapted to determine the desired heat sink parameter based on the model, the provided first heat source parameter and the first temperature distribution, and
the temperature distribution determination unit is adapted to determine, during the second heating period, the second temperature distribution within the object based on the model, the provided second heat source parameter and the desired heat sink parameter.

9. The temperature distribution determination apparatus as defined in claim 8, further comprising:
a temperature sensing element for sensing, in the second heating period, a temperature of the object within a temperature range in which the temperature is not measurable by the temperature distribution measuring unit, wherein the temperature distribution determination unit is further adapted to determine, in the second heating period, the second temperature distribution within the object based on the model, the provided second heat source parameter, the desired heat sink parameter and a sensed temperature of the object sensed by the temperature sensing element.

10. A heating system, including a temperature distribution determination apparatus as defined in claim 7, for heating the object that comprises the heat sink, the heating system comprising:
the heat source for heating the object, and
the temperature distribution determination apparatus for determining the temperature distribution within the object caused by heating the object.

11. The heating system as defined in claim 10, wherein the heating system further comprises a heating control unit for controlling the heat source depending on the temperature distribution.

12. A non-transitory computer readable medium comprising a computer program for causing a heat sink parameter determination apparatus as defined in claim 1 to determine the desired heat sink parameter of a heat sink within the object, out a series of steps of a heat sink parameter determination method when the wherein when executed the heat sink parameter determination method comprises:
providing, via the heat source parameter providing unit, the heat source parameter of the heat source, which defines the heating of the object,
providing, via the model providing unit, the model describing the first temperature distribution in the object, while the object is heated by the heat source, wherein the model depends on (i) one or several heat sink parameters of the heat sink, other than the desired heat sink parameter, which define a cooling of the object while the object is heated, and (ii) the heat source parameter, characterized by
providing, via the heat sink location providing unit, the heat sink location,
measuring, via the temperature distribution measuring unit, the second temperature distribution in the object close to the heat sink location but not at the heat sink location itself, wherein close to the heat sink location includes only parts of the object having a distance to the heat sink location which is equal to or smaller than a predefined distance from the heat sink location, but not at the heat sink location itself, wherein the predefined distance is selected from the group consisting of 3 cm, 2 cm, and 1 cm, and
determining, via the parameter determination unit, the desired heat sink parameter by minimizing the deviation between (i) the second temperature distribution, which has been measured close to the heat sink location which includes only parts of the object having the distance to the heat sink location which is equal to or smaller than the predefined distance from the heat sink location, but not at the heat sink location itself, and (ii) the first temperature distribution that comprises the modeled temperature distribution, wherein the modeled temperature distribution is modeled, via the model provided by the model providing unit, based on (a) the provided heat source parameter and (b) the one or several heat sink parameters, other than the desired heat sink parameter.

13. A non-transitory computer readable medium comprising a computer program for causing a temperature distribution determination apparatus as defined in claim 7 to determine a temperature distribution within the object that comprises the heat sink, wherein the desired heat sink parameter defines the cooling of the object while the object is heated by the heat source, wherein when executed the temperature distribution determination method comprises: determining the heat sink parameter of the heat sink, wherein determining the heat sink parameter comprises
providing, via the heat source parameter providing unit, the heat source parameter of the heat source, which defines the heating of the object,
providing, via the model providing unit, the model describing the first temperature distribution in the object, while the object is heated by the heat source, wherein the model depends on (i) one or several heat sink parameters of the heat sink which define the cooling of the object while the object is heated, and (ii) the heat source parameter, characterized by
providing, via the heat sink location providing unit, the heat sink location,
measuring, via the temperature distribution measuring unit, the second temperature distribution in the object close to the heat sink location, but not at the heat sink location itself, wherein close to the heat sink location includes only parts of the object having the distance to the heat sink location which is equal to or smaller than the predefined distance from the heat sink location, but not at the heat sink location itself, wherein the predefined distance is selected from the group consisting of 3 cm, 2 cm, and 1 cm, and
determining, via the parameter determination unit, the desired heat sink parameter by minimizing the deviation between (i) the second temperature distribution, which has been measured close to the heat sink location which includes only parts of the object having the distance to the heat sink location which is equal to or smaller than the predefined distance from the heat sink location, but not at the heat sink location itself, and (ii) the first temperature distribution that comprises the modeled temperature distribution, wherein the modeled temperature distribution is modeled, via the model provided by the model providing unit, based on (a) the provided heat source parameter and (b) the one or several heat sink parameters; and
determining, via the temperature distribution determination unit, the first temperature distribution within the object based on the model provided by the model providing unit, the heat source parameter provided by the heat source parameter providing unit and the desired heat sink parameter.

14. A heat sink parameter determination method for determining a desired heat sink parameter of a heat sink within an object, the heat sink parameter determination method comprising:
providing, via a heat source parameter providing unit, a heat source parameter of a heat source, which defines a heating of the object,
providing, via a model providing unit, a model describing a first temperature distribution in the object, while the object is heated by the heat source, wherein the model depends on (i) one or several heat sink parameters of the heat sink, other than the desired heat sink parameter, which define a cooling of the object while the object is heated, and (ii) the heat source parameter, characterized by
providing, via a heat sink location providing unit, a heat sink location,
measuring, via a temperature distribution measuring unit, a second temperature distribution in the object close to the heat sink location, but not at the heat sink location itself, wherein close to the heat sink location includes only parts of the object having a distance to the heat sink location which is equal to or smaller than a predefined distance from the heat sink location, but not at the heat sink location itself, wherein the predefined distance is selected from the group consisting of 3 cm, 2 cm, and 1 cm, and determining, via a parameter determination unit, the desired heat sink parameter by minimizing a deviation between (i) the second temperature distribution, which has been measured close to the heat sink location which includes only parts of the object having the distance to the heat sink location which is equal to or smaller than the predefined distance from the heat sink location, but not at the heat sink location itself, and (ii) the first temperature distribution that comprises a modeled temperature distribution, wherein the modeled temperature distribution is modeled, via the model provided by the model providing unit, based on (a) the provided heat source parameter and (b) the one or several heat sink parameters, other than the desired heat sink parameter.

15. A temperature distribution determination method, including a heat sink parameter determination method as defined in claim 14, for determining a temperature distribution within the object that comprises the heat sink, the temperature distribution determination method comprising:

determining the heat sink parameter of the heat sink, and determining, via a temperature distribution determination unit, the first temperature distribution within the object based on the model provided by the model providing unit, the heat source parameter provided by the heat source parameter providing unit and the desired heat sink parameter.

* * * * *